United States Patent [19]

Baichwal

[11] Patent Number: 6,039,980
[45] Date of Patent: Mar. 21, 2000

[54] SUSTAINED RELEASE EXCIPIENT

[75] Inventor: Anand R. Baichwal, Wappinger Falls, N.Y.

[73] Assignee: Edward Mendell Co., Inc., Patterson, N.Y.

[21] Appl. No.: 09/124,576

[22] Filed: Jul. 29, 1998

Related U.S. Application Data

[63] Continuation of application No. PCT/US97/03455, Jan. 29, 1997
[60] Provisional application No. 60/010,722, Jan. 29, 1996.

[51] Int. Cl.⁷ ................................................. A61K 9/20
[52] U.S. Cl. ......................... 424/500; 424/465; 424/468
[58] Field of Search ................................. 424/457, 452, 424/465, 468, 485, 488, 500, 489

[56] References Cited

U.S. PATENT DOCUMENTS

| | | | |
|---|---|---|---|
| 3,405,071 | 10/1968 | Reyes | 252/316 |
| 3,821,414 | 6/1974 | Monti | 424/361 |
| 3,900,569 | 8/1975 | Monti | 424/361 |
| 3,987,204 | 10/1976 | Monti | 424/361 |
| 4,163,777 | 8/1979 | Mitra | 424/21 |
| 4,303,691 | 12/1981 | Sand et al. | 426/573 |
| 4,309,405 | 1/1982 | Guley et al. | 424/21 |
| 4,363,669 | 12/1982 | Cottrell et al. | 106/205 |
| 4,610,870 | 9/1986 | Jain et al. | 424/19 |
| 4,623,394 | 11/1986 | Nakamura et al. | 106/122 |
| 4,689,219 | 8/1987 | Sugden | 424/80 |
| 4,698,264 | 10/1987 | Steinke | 428/402.2 |
| 4,717,713 | 1/1988 | Zatz et al. | 514/2 |
| 4,717,723 | 1/1988 | Sugden | 514/224 |
| 4,762,702 | 8/1988 | Gergely et al. | 424/44 |
| 4,764,380 | 8/1988 | Urquhart et al. | 424/465 |
| 4,765,984 | 8/1988 | Vellekoop et al. | 424/441 |
| 4,784,858 | 11/1988 | Ventouras | 424/468 |
| 4,792,452 | 12/1988 | Howard et al. | 424/475 |
| 4,795,642 | 1/1989 | Cohen et al. | 424/455 |
| 4,814,178 | 3/1989 | Bolton et al. | 424/467 |
| 4,824,675 | 4/1989 | Wong et al. | 424/438 |
| 4,829,056 | 5/1989 | Sugden | 514/54 |
| 4,855,143 | 8/1989 | Lowey | 424/468 |
| 4,857,331 | 8/1989 | Shaw et al. | 424/440 |
| 4,863,742 | 9/1989 | Panoz et al. | 424/473 |
| 4,886,669 | 12/1989 | Ventouras | 424/469 |
| 4,888,177 | 12/1989 | Gergely et al. | 424/466 |
| 4,894,232 | 1/1990 | Reiil et al. | 424/439 |
| 4,915,948 | 4/1990 | Gallopo et al. | 424/435 |
| 4,942,040 | 7/1990 | Ragnarsson et al. | 424/486 |
| 4,948,580 | 8/1990 | Browning | 424/78 |
| 4,968,508 | 11/1990 | Oren et al. | 424/468 |

(List continued on next page.)

FOREIGN PATENT DOCUMENTS

| | | | |
|---|---|---|---|
| 1316108 | 4/1993 | Canada | A61K 9/22 |
| 1330041 | 6/1994 | Canada | A61K 9/22 |
| 0009858 | 4/1980 | European Pat. Off. | A61K 9/16 |
| 0180364 | 5/1986 | European Pat. Off. | A61K 31/54 |
| 0181564 | 5/1986 | European Pat. Off. | A61K 31/19 |
| 0182772 | 5/1986 | European Pat. Off. | A61K 9/22 |
| 0234670 | 9/1987 | European Pat. Off. | A61K 9/22 |
| 0265116 | 4/1988 | European Pat. Off. | A61K 31/725 |
| 0299877 | 1/1989 | European Pat. Off. | A61K 9/22 |
| 0311582 | 4/1989 | European Pat. Off. | A61K 9/22 |
| 0341745 | 11/1989 | European Pat. Off. | A61K 31/725 |
| 0452268 | 10/1991 | European Pat. Off. | A61K 9/50 |
| 0360562 | 7/1993 | European Pat. Off. | A61K 9/22 |
| 0642785 | 3/1995 | European Pat. Off. | A61K 9/22 |
| 2138492 | 1/1973 | France | A61K 27/00 |
| 61-122211 | 6/1986 | Japan | A61K 9/70 |
| 1318169 | 5/1973 | United Kingdom | A61K 27/12 |
| 2162528 | 2/1986 | United Kingdom | A61K 9/22 |
| 2165451 | 4/1986 | United Kingdom | A61K 9/20 |
| 2188843 | 10/1987 | United Kingdom | A61K 9/22 |
| 2264866 | 9/1993 | United Kingdom | A61K 9/08 |
| 8705212 | 9/1987 | WIPO | A61K 9/22 |
| 9003165 | 4/1990 | WIPO | |
| 9513055 | 5/1995 | WIPO | A61K 9/22 |

OTHER PUBLICATIONS

Remington's Pharmaceutical Sciences, Philadelphia College of Pharmacy and Science, 17$^{th}$ Edition, 1985, Ch. 90, pp. 1604–1615, 1625–1626.

H.M. Ingani, et al., 6$^{th}$ Pharmaceutical Technology Conference, vol. II, pp. 459–460, Canterbury, England 1987.

Utilization of Xanthan Gum in the Formulation of Hydrophilic Matrices, H. M. Ingani et A.J. Moes, S.T. Pharma 4 (3) pp. 188–195, 1988 (with translation).

Release Mechanisms in Gelforming Sustained Release Preparations, Bamba, et al., International Journal of Pharmaceutics, 2 (1979) pp. 307–315.

Effect of Third Component Addition on Gel Structure of Interacting Heterodisperse Polysaccharides, C.L. Challinger, et al. Apr. 27, 1993.

John N. Staniforth et al., "Synergistically Interacting Heterodisperse Polysaccharides", Chaphter 24, American Chemical Society, 1993.

Kelco, "Xanthan Gum, Natural Biogum for Scientific Water Control", Fourth Edition, 1988.

J.N. Staniforth et al., "Mono–/Bi Phasic Release Using Heterodisperse Polysaccharides", Proceed. Intern. Symp. Control. Rel. Bioact Mater., 18 (1991).

J.N. Staniforth, et al., "Semi–Quantitative Analysis of Penetrant & Drug Solution Transport in a Hydrogel", Proceed. Intern. Symp. Control. Rel. Bioact. Mater., 18 (1991).

R.L. Davidson, Handbook of Water–Soluble Gums and Resins, McGraw–Hill Book Company, 1980, Chapter 14, pp. 1–16 and Chapter 24, pp. 1–23.

M. Nakano et al., Examination of Natural Gums as Matrices For Sustained Release of Theophylline, Chem. Pharm. Bull. 32(2) 782–785 (1984), pp. 782–785.

*Primary Examiner*—Thurman K. Page
*Assistant Examiner*—Alysia Berman
*Attorney, Agent, or Firm*—Davidson, Davidson & Kappel, LLC

[57] ABSTRACT

A sustained-release formulation for use in oral solid dosage forms includes from about 10 to about 40 percent or more by weight galactomannan gum; from about 1 to about 20 percent by weight of an ionizable gel strength enhancing agent and an inert pharmaceutical filler.

20 Claims, No Drawings

U.S. PATENT DOCUMENTS

| | | | |
|---|---|---|---|
| 4,994,276 | 2/1991 | Baichwal et al. | 424/440 |
| 5,032,406 | 7/1991 | Dansereau et al. | 424/472 |
| 5,047,244 | 9/1991 | Sandvordeker et al. | 424/435 |
| 5,077,051 | 12/1991 | Gallopo et al. | 424/435 |
| 5,110,605 | 5/1992 | Acharya | 424/487 |
| 5,128,143 | 7/1992 | Baichwal et al. | 424/464 |
| 5,132,116 | 7/1992 | Sournac et al. | 424/469 |
| 5,135,757 | 8/1992 | Baichwal et al. | 424/465 |
| 5,169,639 | 12/1992 | Baichwal et al. | 424/488 |
| 5,192,802 | 3/1993 | Rencher | 514/535 |
| 5,271,943 | 12/1993 | Bogart et al. | 424/484 |
| 5,271,946 | 12/1993 | Hettche | 424/490 |
| 5,330,761 | 7/1994 | Baichwal | 424/469 |
| 5,330,763 | 7/1994 | Gole et al. | 424/484 |
| 5,399,358 | 3/1995 | Baichwal et al. | 424/464 |
| 5,399,359 | 3/1995 | Baichwal | 424/464 |
| 5,399,362 | 3/1995 | Baichwal et al. | 424/488 |
| 5,419,917 | 5/1995 | Chen et al. | 429/469 |
| 5,455,046 | 10/1995 | Baichwal | 424/457 |
| 5,472,711 | 12/1995 | Baichwal | 424/468 |
| 5,478,574 | 12/1995 | Baichwal et al. | 424/485 |
| 5,512,297 | 4/1996 | Baichwal | 424/451 |
| 5,554,387 | 9/1996 | Baichwal | 424/488 |
| 5,612,053 | 3/1997 | Baichwal et al. | 424/440 |
| 5,651,987 | 7/1997 | Fuisz | 424/488 |
| 5,662,933 | 9/1997 | Baichwal et al. | 424/457 |
| 5,667,801 | 9/1997 | Baichwal | 424/457 |
| 5,773,025 | 6/1998 | Baichwal | 424/458 |
| 5,846,563 | 12/1998 | Baichwal | 424/457 |

«SUSTAINED RELEASE EXCIPIENT

This application is a continuation application of PCT/US97/03455 filed Jan. 29, 1997, which in turn claims priority from U.S. Provisional Application Ser. No. 60/010,722 filed Jan. 29, 1996.

FIELD OF THE INVENTION

The present invention relates to sustained release excipient formulations which may be blended with a wide range of therapeutically active medicaments and made into sustained release oral solid dosage forms.

BACKGROUND OF THE INVENTION

In our U.S. Pat. Nos. 4,994,276; 5,128,143; and 5,135,757, hereby incorporated by reference, we reported that a controlled release excipient which is comprised of synergistic heterodisperse polysaccharides (e.g., a heteropolysaccharide such as xanthan gum in combination with a polysaccharide gum capable of cross-linking with the heteropolysaccharide, such as locust bean gum) is useful in the preparation of oral solid dosage forms using either direct compression (e.g., following addition of drug and optionally lubricant powder), conventional wet granulation, or a combination of the two. The release of the medicament from the formulations therein proceeds according to zero-order or first-order mechanisms.

The sustained release excipients disclosed in U.S. Pat. Nos. 4,994,276, 5,128,143, and 5,135,757 are commercially available under the tradename TIMERx™ from Edward Mendell Co., Inc., Patterson, N.Y., the assignee of the present invention.

European Patent No. 234670 B (Pankhania et al.) describes a sustained release pharmaceutical formulation containing xanthan gum wherein the xanthan gum comprises from about 7.5 to about 28%, by weight, of the formulation except for a formulation wherein the sustained release carrier comprises a mixture of 15–50 parts by weight dimethylsiloxane, 30–100 parts by weight silicic acid, 30–100 parts by weight mannans or galactans or a mixture thereof, 50–150 parts by weight xanthans and 5–75 parts by weight micronized seaweed.

OBJECTS AND SUMMARY OF THE INVENTION

It is an object of the present invention to provide sustained release formulations which may incorporate a wide range of therapeutically active medicaments.

It is an object of the present invention to provide new sustained release excipient which, when incorporated into a final product, provide a release of therapeutically active medicaments over an extended period of time when the dosage form is exposed to fluids in an environment of use, e.g. from about 12 to about 24 hours or more.

In accordance with the above-mentioned object and disclosure, the present invention is related to sustained release oral solid dosage forms comprising a therapeutically effective amount of a medicament and a sustained release excipient comprising from about 10 to about 40 percent of a galactomannan by weight of the sustained release excipient; from about 1 to about 20 weight percent of an ionizable gel strength enhancing agent by weight of excipient wherein the ratio of the galactomannan to the ionizable gel strength enhancing agent is from about 1:1 to about 3.5:1; from about 60 to about 85 percent by weight of an inert pharmaceutical diluent.

The present invention is also related to sustained-release excipients for use in oral solid dosage forms, comprising from about 10 to about 40 percent or more by weight of a gelling agent; an ionizable gel strength enhancing agent; and an inert pharmaceutical filler. In preferred embodiments, the ionizable gel strength enhancing agent comprises from about 1 to about 20 percent by weight of the sustained release excipient. In additional preferred embodiments, the inert pharmaceutical filler comprises from about 60 to about 85 percent by weight of the sustained release excipient.

In certain preferred embodiments, the sustained release excipient further comprises a hydrophobic material, for example, ethylcellulose. In other preferred embodiments, the ingredients of the sustained release excipient are pre-manufactured as agglomerated particles comprising the homopolysaccharide, the ionizable gel strength enhancing agent, the inert filler, and optional hydrophobic material.

The sustained-release excipient of the present invention can be mixed with a wide range of therapeutically active medicaments and thereafter compressed into solid dosage forms such as tablets. The solid dosage forms thus made slowly release the medicament over about a 24-hour time period when ingested and exposed to an environment of use, e.g. gastric fluids. By varying the amount of excipient relative to the medicament, a desired sustained release profile can be attained.

In a preferred embodiment, the sustained release excipient is present as from about 1 to about 99% by weight of the final formulation. In other preferred embodiments, the sustained release excipient is present as from about 30 to about 90% by weight of the final formulation.

In preferred embodiments, the gelling agent comprises a homopolysaccharide gum. In additional preferred embodiments the homopolysaccharide gum comprises locust bean gum.

In other preferred embodiments, the ionizable gel strength enhancing agent is calcium sulfate.

The present invention also provides a sustained-release formulation comprising a gelling agent, an ionizable gel strength enhancing agent, and an inert pharmaceutical filler, together with an effective amount of a therapeutically active medicament.

In addition, the present invention provides a method for providing a oral sustained release matrix for sustained release dosage forms containing one or more therapeutically active medicaments, comprising preparing a sustained-release matrix by blending the requisite amounts of gelling agent, inert pharmaceutical filler, and ionizable gel strength enhancing agent. In certain preferred embodiments the sustained release excipient is prepared by dry blending the requisite amounts of gelling agent, inert pharmaceutical filler, and gel ionizable strength enhancing agent, wet granulating the mixture, and then drying the mixture to obtain the final sustained release excipient. The sustained release excipient thereby obtained may then be directly admixed with a therapeutically active medicament along with any further pharmaceutically necessary inert excipients, and then formulated into a final oral solid dosage form.

After admixture with the therapeutically active medicaments, the sustained release excipient/drug mixture may then be manufactured into a final dosage form, e.g., by directly compressing the mixture into tablets. The sustained release excipient of the present invention may be used in the manufacture of sustained release oral tablets, buccal tablets, suppositories, granulations, or multi-particulate formulations which may or may not be encapsulated.

DETAILED DESCRIPTION OF THE INVENTION

The sustained release excipients of the invention provides a product which contains a combination of ingredients in preselected proportions to each other which provides a desired sustained release profile over, e.g., a 12 or 24-hour period for a wide variety of drugs. Thus, once the excipient product is admixed with an active medicament (and preferably with a lubricant) in a ratio to the sustained release excipient in accordance with the present invention, the resulting mixture may be made into oral solid dosage forms capable of releasing an active medicament over an extended period of time.

The homopolysaccharide gums used in the present invention include the galactomannans, i.e., polysaccharides which are composed solely of mannose and galactose. Galactomannans which have higher proportions of unsubstituted mannose are preferred in certain embodiments. Locust bean gum, which has a higher ratio of mannose to the galactose, is especially preferred as compared to other galactomannans such as guar and hydroxypropyl guar.

The ionizable gel strength enhancing agent may be monovalent divalent, or multivalent ionizable salts. Preferred salts are the inorganic salts, including various alkali metal and/or alkaline earth metal sulfates, chlorides, borates, bromides, etc. Ionizable alkaline earth organic salts such as citrates, acetates, lactates, etc. may also be used in accordance with the present invention. Specific examples of suitable ionizable gel strength enhancing agents include calcium sulfate, sodium chloride, potassium sulfate, sodium carbonate, lithium chloride, tripotassium phosphate, sodium borate, potassium bromide, potassium fluoride, sodium bicarbonate, calcium chloride, magnesium chloride, sodium citrate, sodium acetate, calcium lactate, magnesium sulfate, alkali metal chlorides, sodium fluoride, organic acids such s citric, succinic, fumaric, malic, maleic, glutaric, lactic and the like; alkali metal sulfates such as sodium sulfate; dihydrogen sodium phosphate, monohydrogen sodium phosphate, disodium hydrogen phosphate, and mixtures thereof. Multivalent metal cations may also be utilized. However, the preferred ionizable gel strength enhancing agents are bivalent. Particularly preferred salts are calcium sulfate and sodium chloride.

In other embodiments of the invention, the ionizable gel strength enhancing agent may comprise a surfactant or wetting agent such as pharmaceutically acceptable anionic surfactants, cationic surfactants, amphoteric (amphipathic/amphophilic) surfactants, and non-ionic surfactants. Examples of suitable surfactant or wetting agents include alkali metal sulfates wherein the alkyl group is from 1 to 14 carbon atoms, such as sodium methyl sulfate, sodium lauryl sulfate and the like as well as dioctyl sodium sulfosuccinate.

It is to be understood that the ionizable compound may be a single compound or a mixture of two or more materials that provide the desired release characteristics. Other examples of suitable surfactants and/or suitable wetting agents are disclosed in U.S. Pat. No. 5,478,574, assigned to the assignee of the present invention, and hereby incorporated by reference.

The ionizable gel strength enhancing agents of the present invention are added in an amount effective to obtain a desirable increased gel strength of a gel formed by exposure of the homopolysaccharide to an aqueous environment.

In the present invention, it has been discovered that the sustained release properties of the dosage forms are optimized when the ratio of the homopolysaccharide gum to ionizable gel strength enhancing agent (e.g., calcium sulfate, etc.) is from about 1:1 to about 3.5:1 and most preferably from about 1.5:1 to about 3:1. Locust bean gum in an amount of from about 15 to about 30 percent or more by weight of the sustained release excipient provides an acceptable sustained release product.

In one preferred embodiment, the ionizable gel strength enhancing agent comprises calcium sulfate, and is present in the sustained release excipient in an amount of about 10 percent, by weight of the excipient. In this embodiment, the ratio of the homopolysaccharide to the ionizable gel strength enhancing agent is preferably from about 1.5:1 to about 3:1.

Any generally accepted soluble or insoluble inert pharmaceutical filler (diluent) material can be used. Preferably, the inert pharmaceutical filler comprises a monosaccharide, a disaccharide, a polyhydric alcohol, a cellulose (such as microcrystalline cellulose) and/or mixtures thereof. Examples of suitable inert pharmaceutical fillers include sucrose, dextrose, lactose, microcrystalline cellulose, xylitol, fructose, sorbitol, starches, mixtures thereof and the like. However, it is preferred that a soluble pharmaceutical filler such as dextrose, sucrose, or mixtures thereof be used.

In certain preferred embodiments of the invention, the sustained release matrix further comprises a hydrophobic material in an amount effective to slow the hydration of the gum without disrupting the hydrophilic matrix formed by the homopolysaccharide when the formulation is exposed to fluids in an environment of use. This may be accomplished is by granulating the sustained release matrix with a solution or dispersion of hydrophobic material prior to the incorporation of the medicament. The hydrophobic material may be selected from alkylcelluloses, acrylic and/or methacrylic acid polymers or copolymers, hydrogenated vegetable oils, zein, as well as other pharmaceutically acceptable hydrophobic materials known to those skilled in the art. A preferred hydrophobic cellulosic material is ethylcellulose. The amount of hydrophobic material incorporated into the sustained release matrix is that which is effective to slow the hydration of the gums without disrupting the hydrophilic matrix formed upon exposure to an environmental fluid, e.g. an aqueous environment.

In certain preferred embodiments of the present invention, the hydrophobic material may be included in the sustained release excipient in an amount from about 1to about 20% by weight. More preferably, the hydrophobic material may be included in the sustained release matrix in an amount from about 3% to about 12%, and most preferably from about 5% to about 10%, by weight of the final formulation. The hydrophobic material may be dissolved in an organic solvent or dispersed in an aqueous solution for incorporation into the formulation.

In other embodiments, all or a portion of the hydrophobic material may be applied to the final dosage form, e.g a tablet, as a sustained-release coating.

The combination of the homopolysaccharide (e.g., locust bean gum) with the ionizable gel strength enhancing agent and inert diluent provides a ready to use sustained release excipient in which a formulator need only blend the desired active medicament and an optional lubricant with the excipient and then make an oral solid dosage form. The sustained release excipient may thus comprise a physical admix of the homopolysaccharide along with an ionizable gel strength enhancing agent, or soluble excipient such as sucrose, lactose or dextrose.

One of the limitations of direct compression as a method of tablet manufacture is the size of the tablet. For example, where the dosage form is an oral sustained release tablet and the dose of therapeutically active agent to be contained in the tablet is relatively large, a pharmaceutical formulator may choose to wet granulate the drug with other excipients to attain a desired tablet size with the correct compact strength (e.g., hardness). Usually the amount of filler/binder or excipients needed in wet granulation is less than that in direct compression since the process of wet granulation contributes to some extent toward the desired physical properties of a tablet. Accordingly, the ingredients of the sustained release pharmaceutical excipient prepared in accordance with the present invention may be subjected to wet granulation before the medicament is added. In this technique, the desired amounts of the homopolysaccharide, the ionizable gel strength enhancing agent, and the inert filler are mixed together and thereafter a moistening agent such as water, propylene glycol, glycerol, alcohol or the like is added to prepare a moistened mass. Next, the moistened mass is dried. The dried mass is then milled with conventional equipment into granules. Therefore, the sustained-release excipient product is ready to use. The granulate thus obtained has certain advantages including the fact that it is free-flowing, has good cohesive properties, and can be admixed with an active agent (e.g., drug) and can be directly compressed into tablets. On the other hand, the granulate can be formulated into a capsule, used in the granulate form, extruded, and/or spheronized with an active medicament to form pellets, etc. In alternative preferred embodiments, the ingredients of the sustained release excipient may be wet granulated with all or part of the therapeutically active agent. The active agent may be added in crystalline or amorphous form.

Alternatively, the medicament may be wet-granulated in appropriate circumstances with one or more of the ingredients of the sustained release excipient. The remaining release excipient ingredients can simply be admixed to the resultant pre-granulated material or granulated together with the pre-granulated ingredients in a second wet granulation step.

Alternatively, it is possible in certain embodiments to dry mix the ingredients of the sustained release excipient without utilizing a wet granulation step. This procedure may be utilized, for example, where a wet granulation step is to be accomplished when the active ingredient is directly added to the ingredients of the sustained release excipient. On the other hand, this procedure may also be used where no wet granulation step whatsoever is contemplated. If the mixture is to be manufactured without a wet granulation step, and the final mixture is to be tableted, it is preferred that all or part of the inert diluent comprise a pre-manufactured direct compression diluent. Such direct compression diluents are widely used in the pharmaceutical arts, and may be obtained from a wide variety of commercial sources. Examples of such pre-manufactured direct compression excipients include Emcocel® (microcrystalline cellulose, N.F.), Emdex® (dextrates, N.F.), and Tab-Fine® (a number of direct compression sugars including sucrose, fructose, and dextrose), all of which are commercially available from Edward Mendell Co., Inc., Patterson, N.Y.). Other direct compression diluents include Anhydrous lactose (Lactose N.F., anhydrous direct tableting) from Sheffield Chemical, Union, N.J. 07083; Elcems® G-250 (Powdered cellulose, N.F.) from Degussa, D-600 Frankfurt (Main) Germany; Fast-Flo Lactose® (Lactose, N.F., spray dried) from Foremost Whey Products, Banaboo, WI 53913; Maltrin® (Agglomerated maltrodextrin) from Grain Processing Corp. Muscatine, Iowa 52761; Neosorb 60® (Sorbitol, N.F., direct compression) from Roquette Corp., 645 5th Ave., New York, N.Y, 10022; Nu-Tab® (Compressible sugar, N.F.) from Ingredient Technology, Inc., Pennsauken, N.J. 08110; Polyplasdone XL® (Crospovidone, N.F., cross-linked polyvinylpyrrolidone) from GAF Corp., New York, N.Y. 10020; Primojel® (Sodium starch glycolate, N.F., carboxymethyl starch) from Generichem Corp., Little Falls, N.J. 07424; Solka Floc® (Cellulose floc) from Edward Mendell Co., Carmel, N.Y. 10512; Spray-dried lactose® (Lactose N.F., spray dried) from Foremost Whey Products, Banaboo, Wis. 53913 and DMV Corp., Vehgel, Holland; and Sta-Rx 1500® (Starch 1500) (Pregelatinized starch, N.F., compressible) from Colorcon, Inc., West Point, Pa. 19486.

Finally, in further alternative embodiments of the invention, a therapeutically active agent can be incorporated (admixed, granulated, etc.) with any of the ingredients of the sustained release excipient, if so desired. The remaining formulation steps would remain essentially the same as would be understood by one skilled in the art.

In general, the formulator may prepare a directly compressible diluent, by wet granulating or spray drying lactose, for example. For purposes of the present invention, these specially treated inert diluents will be referred to as "directly compressible" inert diluents In further embodiments of the present invention, the directly compressible inert diluent which is used in conjunction with the sustained release pharmaceutical excipient of the present invention is an augmented microcrystalline cellulose as disclosed in U.S. Pat. application Ser. No. 08/370, 576, filed Jan. 9, 1995, and entitled "PHARMACEUTICAL EXCIPIENT HAVING IMPROVED COMPRESSIBILITY", inventors B. Sherwood, J. Staniforth, and E. Hunter, hereby incorporated by reference now U.S. Pat. No. 5,585,115.

Once the sustained release excipient of the present invention has been prepared, it is then possible to blend the same with an active medicament, metoprolol, e.g., in a V-blender. The mixture may then be manufactured into the desired final dosage form. If desired, the mixture can be directly compressed into tablets, or subjected to other intermediate processing steps such as wet granulation.

The dosage forms of the present invention are preferably tablets. However, the ingredients may also be formulated in a capsule, extruded and spheronized with an active medicament to form pellets, etc.

For example, the complete mixture, in an amount sufficient to make a uniform batch of tablets, is then subjected to tableting in a conventional production scale tableting machine at normal compression pressure, i.e. about 2000–1600 lbs/sq in. However, the mixture should not be compressed to such a degree that there is subsequent difficulty in its hydration when exposed to gastric fluid. An effective amount of any generally accepted pharmaceutical lubricant, including the calcium or magnesium soaps may be added to the above-mentioned ingredients of the excipient be added at the time the medicament is added, or in any event prior to compression into a said dosage form. One preferred lubricant is Pruv®, e.g., in the amount of about 3.0 percent of the solid dosage form.

The average tablet size for round tablets is preferably about 500 mg to 750 mg and for capsule-shaped tablets about 750 mg to 1000 mg.

The average particle size of the granulated excipient of the present invention ranges from about 50 microns to about 400 microns and preferably from about 185 microns to about 265 microns. The particle size of the granulation is not narrowly critical, the important parameter being that the average particle size of the granules, must permit the formation of a directly compressible excipient which forms pharmaceutically acceptable tablets. The desired tap and bulk densities of the granulation of the present invention are normally between from about 0.3 to about 0.8 g/ml, with an average density of from about 0.5 to about 0.7 g/ml. For best results, the tablets formed from the granulations of the present invention are from about 6 to about 8 kg hardness. The average flow of the granulations prepared in accordance with the present invention are from about 25 to about 40 g/sec.

Variables which may affect the release rate and the compressibility of tablets prepared with the excipient of the present invention are the drug to gum ratio; the method of incorporation of excipient (method of granulation); the relative amount of the gum to ionizable gel strength enhancing agent; and the ratio of active medicament to the sustained-release excipient.

The sustained release excipient formulations of the present invention may be utilized in the preparation of a wide range of 24 hour solid dosage forms which include a wide range of water-soluble or water-insoluble medicaments. Examples of such therapeutically active agents include antihistamines (e.g., dimenhydrinate, diphenhydramine, chlorpheniramine and dexchlorpheniramine maleate), analgesics (e.g., aspirin, codeine, morphine, dihydromorphone, oxycodone, etc.), anti-inflammatory agents (e.g., naproxen, diclofenac, indomethacin, ibuprofen, aspirin, sulindac), acetaminophen, gastro-intestinals and anti-emetics (e.g., metoclopramide), anti-epileptics (e.g., phenytoin, meprobamate and nitrezepam), vasodilators (e.g., nifedipine, papaverine, diltiazem and nicardipine), anti-tussive agents and expectorants (e.g., codeine phosphate), anti-asthmatics (e.g. theophylline), anti-spasmodics (e.g., atropine, scopolamine), hormones (e.g., insulin, heparin), diuretics (e.g., ethacrynic acid, bendroflumethiazide), anti-hypotensives (e.g., propranolol, clonidine), bronchodilators (e.g., albuterol), anti-inflammatory steroids (e.g., hydrocortisone, triamcinolone, prednisone), antibiotics (e.g., tetracycline), antihemorrhoidals, hypnotics, psychotropics, antidiarrheals, mucolytics, sedatives, decongestants, laxatives, antacids, vitamins, stimulants (including appetite suppressants such as phenylpropanolamine). The above list is not meant to be exclusive. The medicaments may be present in the dosage form in, e.g., crystalline or amorphous form.

Upon oral ingestion and contact with gastric fluid, the controlled release formulations prepared according to the present invention swell and gel to form a hydrophilic gel matrix from which the drug is released. In the case of a tablet, the swelling of the matrix causes a reduction in the bulk density of the tablet and provides the buoyancy necessary to allow the gel mass to float on the stomach contents to provide a slow delivery of the medicament. The matrix, the size of which is dependent upon the size of the original tablet, can swell considerably and become obstructed near the opening to the pylorus. Since the medicament is dispersed throughout the tablet (and consequently throughout the gel matrix), a constant amount of drug can be released per unit time in vivo by dispersion or erosion of the outer portions of the matrix. This phenomenon is commonly referred to as a zero order release profile or zero order kinetics. The process continues, with the matrix remaining buoyant in the stomach, until substantially all of the medicament is released. The chemistry of certain of the ingredients comprising the excipients of the present invention such as locust bean gum is such that the excipients are considered to be self-buffering agents which are substantially insensitive to the solubility of the medicament and likewise insensitive to the pH changes along the length of the gastrointestinal tract. Moreover, the chemistry of the ingredients comprising the excipients of the present invention is believed to be similar to certain known mucoadhesive substances such as polycarbophil. Mucoadhesive properties are desirable for buccal delivery systems. Thus, it may be possible that the gel system could potentially loosely interact with the mucin in the gastrointestinal tract and thereby provide another mode by which a constant rate of delivery of the medicament is achieved. The above hypothesis is included for discussion purposes only and is not intended to limit the scope of the present invention.

In formulations where the excipient is used in a suppository, a suitable vehicle must be added to the formulation. Generally, suitable vehicles are non-toxic and non-irritating to mucous membranes, are compatible with a variety of drugs, melt and dissolve in an environment of use, e.g. vaginal or rectal fluids and are stable on storage. A non-exclusive list of suitable vehicles includes synthetic and non-synthetic fatty acids, waxes, cocoa butter, glycerinated gelatin, hydrogenated vegetable oils, mixtures of polyethylene glycol, fatty acid esters, and mixtures thereof. One skilled in the art would understand the amount of vehicle incorporated into a particular suppository formulation will be a pharmaceutically suitable amount determined by a variety of factors, e.g. amount of active agent, vehicle used, etc.

In formulations where the granulation is not compressed, the granulation may be divided into unit doses and placed, e.g. in approximately sized gelatin capsules.

DETAILED DESCRIPTION OF THE PREFERRED EMBODIMENTS

The following examples illustrate various aspects of the present invention. They are not to be construed to limit the claims in any manner whatsoever.

EXAMPLES 1–3

The sustained release excipient is prepared by dry blending the requisite amounts of locust bean gum, dextrose and calcium sulfate in a high-speed mixer/granulator for 2 minutes. While running choppers/impellers, the water is added and the mixture is granulated for another 2 minutes. The granulation is then dried in a fluid bed dryer to a loss on drying weight (LOD) of between 4 and 7%. The granulation is then milled using 20 mesh screens. The ingredients of the sustained release excipient of Examples 1–3 are set forth in Table 1 below:

TABLE 1

| PREPARATION OF SUSTAINED RELEASE EXCIPIENT | | | |
|---|---|---|---|
| Component | %-Ex. 1 | %-Ex. 2 | %-Ex. 3 |
| 1. LBG | 30 | 15 | 30 |
| 2. Dextrose | 60 | 75 | 70 |
| 3. Calcium Sulfate | 10 | 10 | 0 |
| 4. Water | 10* | 10* | 10* |

*removed during processing
LBG = locust bean gum

Next, the sustained release excipient prepared as detailed above is dry blended with a desired amount of medicament (in the following examples metoprolol, provided as the tartrate salt) in a V-blender for 10 minutes. A suitable amount of tableting lubricant Pruv® (sodium stearyl fumarate, NF, commercially available from the Edward Mendell Co., Inc.) for the following examples is added and the mixture is blended for another 5 minutes. This final mixture is compressed into tablets, each tablet containing 100 mg metoprolol. The tablets of Example 1 weighed 618.5 mg. The tablets of Example 2 weighed 618.5 mg. The tablets of Example 3 weighed 618.5 mg. The drug:gum ratio of the tablets of Example 1 was 1:1.5. The drug:gum ratio of the tablets of Example 2 was 1:0.75. The drug:gum ratio of the tablets of Example 3 was 1:1.5. The ingredients of the tablets of Examples 1–3 are set forth in Table 2 below:

TABLE 2

| Component | % |
| --- | --- |
| 1. Sustained Release Excipient | 80.8% |
| 2. Metoprolol | 16.2% |
| 3. Pruv ® | 3.0% |

The examples provided above are not meant to be exclusive. Many other variations of the present invention would be apparent to those skilled in the art, and are contemplated to be within the scope of the appended claims.

What is claimed is:

1. An oral solid dosage form comprising:
   a therapeutically effective amount of a medicament; and
   a sustained release excipient comprising from about 10 to about 40 percent of a gelling agent by weight of said sustained release excipient said gelling agent consisting of a galactomannan, from about 1 to about 20 by weight percent of an ionizable gel strength enhancing agent by weight of said excipient, such that the ratio of said galactomannan to said ionizable gel strength enhancing agents from about 1:1 to about 3.5:1
   and from about 60 to about 85 percent by weight of an inert pharmaceutical diluent by weight of the sustained release excipient.

2. The oral solid dosage form of claim 1, wherein said inert pharmaceutical diluent is selected from the group consisting of lactose, dextrose, sucrose, fructose, microcrystalline cellulose, xylitol, sorbitol, starch and mixtures thereof.

3. The oral solid dosage form of claim 1, wherein the ratio of said inert pharmaceutical diluent to said galactomannan is from about 6:1 to about 2:1.

4. The oral solid dosage form of claim 2, wherein said galactomannan, said ionizable gel strength enhancing agent, and said inert pharmaceutical diluent are agglomerated into granular particles via wet granulation.

5. The oral solid dosage form of claim 1, wherein said ionizable gel strength enhancing agent is selected from the group consisting of calcium sulfate, sodium chloride, potassium sulfate, sodium carbonate, lithium chloride, tripotassium phosphate, sodium borate, potassium bromide, potassium fluoride, sodium bicarbonate, calcium chloride, magnesium chloride, sodium citrate, sodium acetate, calcium lactate, magnesium sulfate, sodium fluoride and mixtures thereof.

6. The oral solid dosage form of claim 1, wherein said ionizable gel strength enhancing agent is calcium sulfate.

7. The oral solid dosage form of claim 1, wherein said galactomannan is locust bean gum.

8. The oral solid dosage form of claim 1, wherein said galactomannan is locust bean gum and said gel strength enhancing agent is calcium sulfate.

9. The oral solid dosage form of claim 1, wherein said sustained release excipient comprises from about 1 to about 99% by weight of the oral dosage form.

10. The oral solid dosage form of claim 1, which is in the form of agglomerated particles.

11. The oral solid dosage form of claim 1, wherein said inert pharmaceutical diluent is directly compressible.

12. The oral solid dosage form of claim 11, wherein said directly compressible diluent is selected from the group consisting of microcrystalline cellulose, dextrates, direct-compression sugars, anhydrous lactose, powdered cellulose, spray dried lactose, agglomerated maltrodextrin, sorbitol, crospovidone, sodium starch glycolate, carboxymethyl starch, cellulose, and pregelatinized starch.

13. The oral solid dosage form of claim 1, further comprising an amount of a hydrophobic material effective to slow the hydration of said galactomannan when exposed to an environmental fluid.

14. The sustained release excipient of claim 13, wherein said hydrophobic material is selected from the group consisting of an alkylcellulose, a copolymer of acrylic and methacrylic acid esters, waxes, shellac, zein, hydrogenated vegetable oils, and mixtures of any of the foregoing.

15. The oral solid dosage form of claim 13, wherein said hydrophobic material comprises from about 1 to about 20 percent weight of said sustained release excipient.

16. The oral solid dosage form of claim 13, wherein said hydrophobic material is ethylcellulose.

17. A sustained release pharmaceutical excipient, comprising:
   from about 10 to about 40% by weight of a gelling agent, said gelling agent consisting of a galactomannan:
   from about 1 to about 20 percent by weight of an ionizable gel strength enhancing agent, such that the ratio of said galactomannan to said ionizable gel strength enhancing agent is from about 1:1 to about 3.5:1; and
   from about 60 to about 85 percent by weight of an inert pharmaceutical diluent.

18. A method for preparing a sustained release excipient, comprising:
   wet granulating a gelling agent consisting of a galactomannan, an ionizable gel strength enhancing agent and an inert pharmaceutical diluent selected from the group consisting of a monosaccharide, a disaccharide, a polyhydric alcohol, a cellulose, a starch, and mixtures thereof, and
   drying the mixture to obtain distinct excipient particles.

19. A method for preparing a sustained release dosage form, comprising:
   incorporating a gelling agent consisting of a galactomannan, an ionizable gel strength enhancing agent, an inert pharmaceutical diluent, and a medicament into a mixture; and
   directly compressing said mixture to form a solid unit dosage form.

20. The method of claim 19 wherein at least two of said galactomannan, said ionizable gel strength enhancing agent, said an inert pharmaceutical diluent, and said medicament are wet granulated together prior to compressing said mixture into a solid oral dosage form.

* * * * *